United States Patent [19]

Moses

[11] 3,973,276

[45] Aug. 10, 1976

[54] INCONTINENT'S BED WRAP

[75] Inventor: Bernice Moses, Rosedale, N.Y.

[73] Assignee: Lawrence Peska Associates, Inc., New York, N.Y.; a part interest

[22] Filed: July 17, 1975

[21] Appl. No.: 596,731

[52] U.S. Cl. .................................. 2/215; 2/DIG. 7
[51] Int. Cl.² ............................................ A41D 1/14
[58] Field of Search ................. 2/114, 105, 109, 73, 2/74, 75, 111, 215, 219, 221, DIG. 6, DIG. 7; 128/132 R, 132 D, 134, 168, 284, 287, 288

[56] References Cited
UNITED STATES PATENTS

| 715,248 | 12/1902 | Davis | 2/75 |
|---|---|---|---|
| 1,823,257 | 9/1931 | Cooper | 2/74 |
| 2,081,915 | 6/1937 | Edmiston | 2/73 |
| 2,637,035 | 5/1953 | Herzog | 2/73 |
| 3,108,599 | 10/1963 | Mammarella | 128/288 X |
| 3,276,036 | 10/1966 | Cater | 2/114 |
| R26,939 | 8/1970 | Hervey et al. | 128/284 |

OTHER PUBLICATIONS

"Velcro Fasteners".

Primary Examiner—Werner H. Schroeder
Assistant Examiner—Moshe I. Cohen
Attorney, Agent, or Firm—Jack D. Slobod

[57] ABSTRACT

An incontinent's bed wrap is generally a trapezoidal sheet of substantially absorbent and water impervious flannelette material which serves as a wrap-around skirt. Snap fasteners are carried at corners bounding the narrowest edge of the sheet for fastening around the waist. A flap is folded over to a back side of the sheet along each edge of the sheet to define a frame for receiving a disposable absorbent pad.

1 Claim, 2 Drawing Figures

INCONTINENT'S BED WRAP

FIELD OF THE INVENTION

The present invention relates generally to clothing articles of protection for incontinents. In its particular aspects, the present invention relates to a wrap-around skirt configured for an incontinent.

BACKGROUND OF THE INVENTION

Various incontinent briefs and panties are presently available for use under bed clothes and hospital gowns. However, since such articles utilize elastic around the legs for proper protection, various problems are presented. In some cases, additional protection is required since worn and stretched elastic permits leakage. In other cases, primarily related to geriatric patients, the tight elastic causes undue interference with blood circulation. Further, because of their configuration, incontinent briefs and panties are difficult to remove and replace.

OBJECTS OF THE INVENTION

It is an object of the present invention to provide an alternative or supplement for incontinent briefs and panties which is an easily removable skirt.

It is a further object of the present invention to provide a means for carrying a disposable absorbent pad for additional absorbtion within a loosely fitting incontinent's bed wrap.

SUMMARY OF THE INVENTION

Briefly, the aforementioned and other objects of the present invention are satisfied by providing an incontinent's bed wrap in the form of a wrap-around skirt of substantially absorbent and water impervious material which skirt is fastenable about the waist. The bed wrap includes on its inside surface a plurality of flaps for capturing a disposable pad of absorbent material for additional absorbency.

The bed wrap is easily removable and loose fitting. It can be worn under bed clothes or a hospital gown replacing or supplementing tightly fitting incontinent briefs and panties.

Other objects, features and advantages of the present invention will become apparent upon perusal of the following detailed description of the preferred embodiment thereof when taken in conjunction with the appended drawing wherein:

FIG. 1 is a plan view of the back side of the bed wrap of the present invention in an open position; and FIG. 2 is a view of the bed wrap in FIG. 1 but in a nearly closed position.

DETAILED DESCRIPTION

Figure 1:
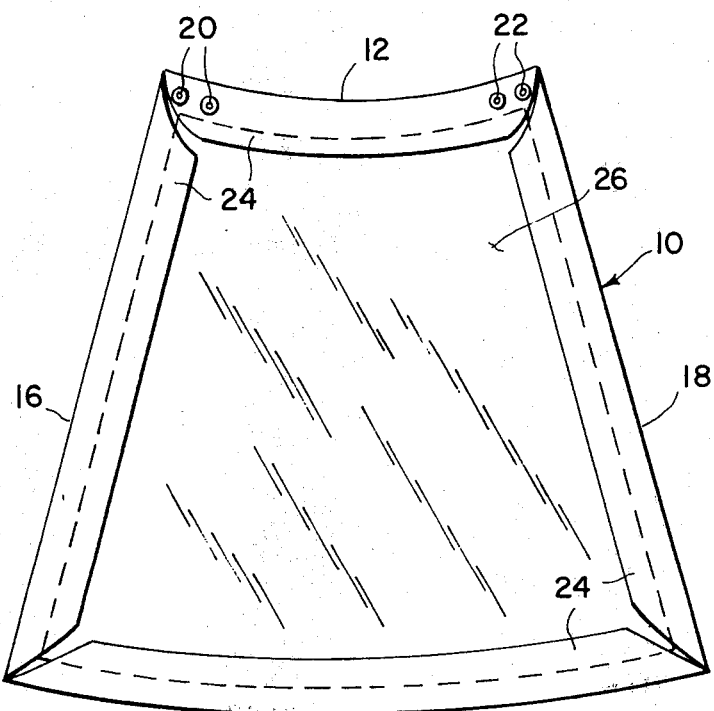
Figure 2:
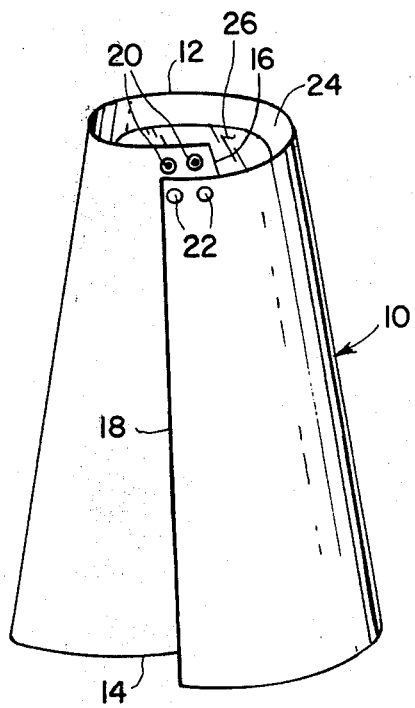

Referring to FIGS. 1 and 2 of the drawing, the incontinent's bed wrap 10 of the present invention comprises a generally trapezoidal shaped sheet of substantially absorbent and water impervious material such as waterproofed flannelette which functions as a wrap-around skirt to be worn under bed clothes or a hospital gown. The wrap 10 includes a narrow top margin 12, a bottom margin 14 and side margins 16 and 18. Pairs of oppositely directed snap fasteners 20 and 22 are respectively carried near the opposite corners of the wrap 10 which bound top margin 12. Snap fasteners 20 and 22 engage each other when the bed wrap 10 is rolled into a wrap-around skirt as shown in FIG. 2. As is apparent, the margin 12 is secured around the waist of an incontinent. The snap fasteners 20 and 22 are provided in pairs to provide an adjustment in waist dimension by allowing different discrete positions of engagement between the fasteners involving different ones or both fasteners in each pair. Alternatively, instead of fasteners 20 and 22, mutually engaging sheets of upstanding hook and eye or hook and hook fasteners (not shown) known under the trademark VELCRO might be utilized to provide a continuous adjustment in the girth of the waist.

As illustrated in FIG. 1, the back side of the wrap 10 which is adapted to face the wearer is provided with four flaps 24 depending along each of the four margins 12, 14, 16 and 18 of the wrap and folded over onto the back side. The flaps 24 provide means for receiving a trapezoidally shaped disposable pad 26 of absorbent material such as layers of paper if additional absorbency is required. The pad 26 lines substantially the entire back side of the wrap 10, the margins of the pad being captured in a frame formed by flaps 24.

The wrap 10 is easily removed from an incontinent by disengaging fasteners 20 and 22 thus allowing pad 26 to be rolled up and replaced with a fresh pad.

The bed wrap 10 being configured as a wrap-around skirt is beneficially used in situations where the tight elastic necessarily utilized in presently available incontinent briefs and panties unduly choke off blood circulation. Also, it may be noted that the bed wrap is preferably washable and therefore reusable.

Having described the preferred embodiment of the present invention in specific detail, it should be apparent that numerous modifications, additions and omissions are possible in the details thereof within the intended spirit and scope of the invention.

What is claimed is:

1. An incontinent's bed wrap skirt comprising: a generally trapezoidal sheet of substantially water impervious material; mutually engageable fastener means carried at a pair of corners bounding a narrowest edge of said sheet for securing said narrowest edge around the waist of a user; said sheet having a back side adapted to face the body of the user; a disposable absorbent pad of trapezoidal shape and of substantially the same size as said sheet; and flaps along each edge of said sheet folded over to said back side forming a peripheral frame for receiving and removeably retaining said pad as a lining along substantially the entire back side of said sheet.

* * * * *